(12) United States Patent
Jarvi et al.

(10) Patent No.: US 8,293,906 B2
(45) Date of Patent: *Oct. 23, 2012

(54) PROCESSES FOR THE ALKYLATION OF NORBUPRENORPHINE WITH REDUCED IMPURITY FORMATION

(75) Inventors: Esa T. Jarvi, Ballwin, MO (US); James R. Meyer, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 469 days.

This patent is subject to a terminal disclaimer.

(21) Appl. No.: 12/586,854

(22) Filed: Sep. 29, 2009

(65) Prior Publication Data

US 2010/0081820 A1    Apr. 1, 2010

Related U.S. Application Data

(60) Provisional application No. 61/194,784, filed on Sep. 30, 2008.

(51) Int. Cl.
*C07D 489/12* (2006.01)
*C07D 489/10* (2006.01)

(52) U.S. Cl. .......................................... 546/39; 546/38

(58) Field of Classification Search ................ 546/39, 546/40, 38
See application file for complete search history.

(56) References Cited

U.S. PATENT DOCUMENTS 7,119,100 B2 * 10/2006 Zhong et al. ................ 514/279
2008/0312441 A1   12/2008   Mannino et al.

FOREIGN PATENT DOCUMENTS

EP    1 439 179 A1    7/2004
GB    1136214    12/1968

OTHER PUBLICATIONS

Lewis, "Rinc C-Bridged Derivatives of Thebaine and Oripavine", Advances in Biochemical Psychopharmacolocy, 1973, 8, pp. 123-136.
Uff et al., "NMR Spectra and Stereochemistry of some 7-Substituted 6,14-Bridged Thebaine Derivatives", Magnetic Resonance in Chemistry, 23(6), 1985, pp. 454-459, XP 002558538.
Archer et al., "Hybromet: A Ligand for Purifying Opioid Receptors", J. Med. Chem., 1985, 28, pp. 1950-1953, XP 002558539.

* cited by examiner

*Primary Examiner* — Charanjit Aulakh

(57) ABSTRACT

The invention provides processes for the production of opiate alkaloids. In particular, the present invention provides processes for the formation of buprenorphine and derivatives of buprenorphine that minimizes the formation of impurities.

20 Claims, No Drawings

PROCESSES FOR THE ALKYLATION OF NORBUPRENORPHINE WITH REDUCED IMPURITY FORMATION

CROSS REFERENCE TO RELATED APPLICATIONS

This application claims priority from U.S. Provisional Application No. 61/194,784, filed on Sep. 30, 2008, which is hereby incorporated by reference in its entirety.

FIELD OF THE INVENTION

The present invention generally relates to processes for the synthesis of buprenorphine and derivatives of buprenorphine. In particular, the present invention provides processes for the formation of these opiate compounds that minimizes the formation of impurities.

BACKGROUND OF THE INVENTION

Buprenorphine hydrochloride and products containing it are effective treatments of opiate addiction. Methods of synthesizing buprenorphine have been known from the late 1960s. For instance, buprenorphine may be synthesized by an alkylation reaction from norbuprenorphine utilizing bromomethylcyclopropane. The bromomethylcyclopropane typically contains an alkenyl impurity which can also participate in the alkylation reaction. This leads to the formation of Impurity A, otherwise known as (2S)-2-[17-(but-3-enyl)-4,5α-epoxy-3-hydroxy-6-methoxy-6α,14-ethano-14α-morphinan-7α-yl]-3,3-dimethylbutan-2-ol. Impurity A is difficult to remove from the final buprenorphine product by known purification techniques, resulting in products with higher impurities than acceptable by the currently prescribed guidelines established by the International Conference on Harmonisation of Technical Requirements for Registration of Pharmaceuticals for Human Use (ICH) and the United States Pharmacopeial Convention (USP). In addition, the typical synthesis uses preparatory chromatography to purify the crude buprenorphine product, which can be costly and labor intensive. Consequently, there is a need in the art for an efficient process for producing buprenorphine with impurity levels that meet or exceed the ICH requirements.

SUMMARY OF THE INVENTION

One aspect of the present invention encompasses a process for the preparation of a compound comprising Formula (II). The process typically comprises forming a reaction mixture by combining a compound comprising Formula (I) with $MCO_3$, a catalytic additive, and $R^1X^1$. Generally, the amount of alkenyl impurity comprising $R^1X^1$ is less than 0.15% by weight. The reaction mixture is heated to a temperature of less than 60° C. to form the compound comprising Formula (II) according to the following reaction scheme:

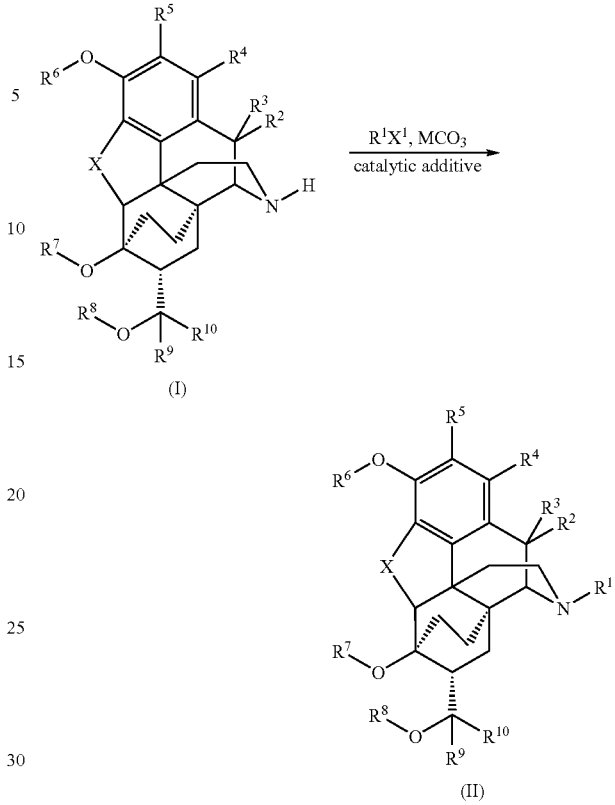

wherein:
- $R^1$ is selected from the group consisting of an alkyl, a substituted alkyl, and a cycloalkyl;
- $R^2$ and $R^3$ are independently selected from the group consisting of hydrogen, hydrocarbyl and substituted hydrocarbyl;
- $R^4$ and $R^5$ are independently selected from the group consisting of hydrogen, hydrocarbyl, substituted hydrocarbyl, halogen, {—}OH, {—}NH$_2$, {—}SH, {—}SR$^{11}$, and {—}OR$^{11}$;
- $R^6$ and $R^7$ are independently selected from the group consisting of hydrogen, a protecting group, hydrocarbyl, and substituted hydrocarbyl;
- $R^8$ is selected from the group consisting of hydrogen, hydrocarbyl, and substituted hydrocarbyl;
- $R^9$, $R^{10}$, and $R^{11}$ are independently selected from the group consisting of hydrocarbyl and substituted hydrocarbyl;
- M is selected from the group consisting of a metal cation having a charge of $^+1$, and a metal cation group having a charge of $^+2$;
- X is a heteroatom; and
- $X^1$ is a halogen.

Another aspect of the invention encompasses a process for the preparation of a compound comprising Formula (IIa). The process comprises forming a reaction mixture by combining a compound comprising Formula (I) with $MCO_3$, a catalytic additive, and cyclopropylmethylbromide. Generally, the cyclopropylmethylbromide comprises less than 0.15% by weight of 4-bromo-1-butene. The reaction mixture is heated to a temperature of less than 60° C. to form the compound comprising Formula (IIa) according to the following reaction scheme;

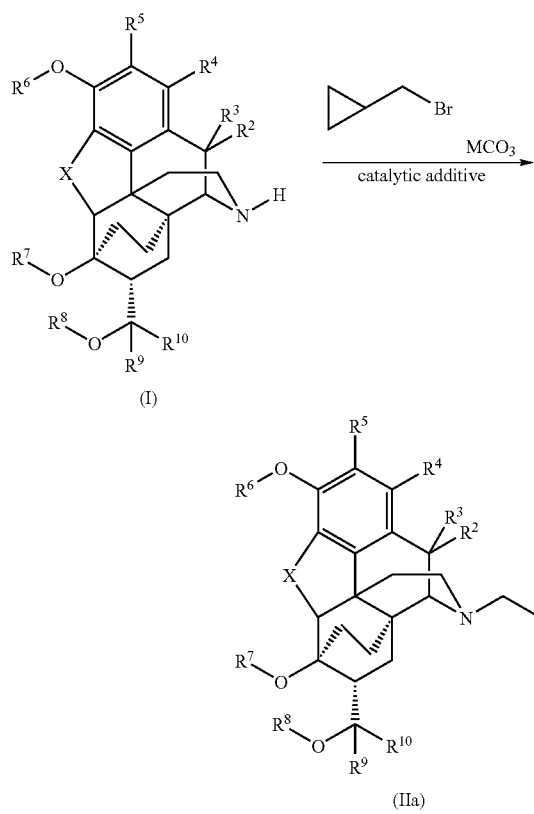

(I)

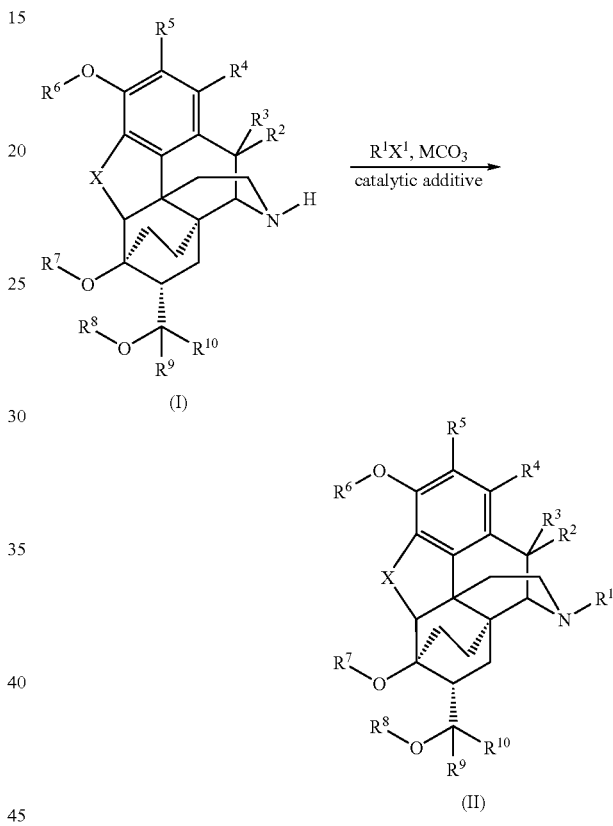

Reaction Scheme 1

(IIa)

wherein:
- $R^2$ and $R^3$ are independently selected from the group consisting of hydrogen, hydrocarbyl and substituted hydrocarbyl;
- $R^4$ and $R^5$ are independently selected from the group consisting of hydrogen, hydrocarbyl, substituted hydrocarbyl, halogen, {—}OH, {—}NH$_2$, {—}SH, {—}SR$^{11}$, and {—}OR$^{11}$;
- $R^6$ and $R^7$ are independently selected from the group consisting of hydrogen, a protecting group, hydrocarbyl, and substituted hydrocarbyl;
- $R^8$ is selected from the group consisting of hydrogen, hydrocarbyl, and substituted hydrocarbyl;
- $R^9$, $R^{10}$, and $R^{11}$ are independently selected from the group consisting of hydrocarbyl and substituted hydrocarbyl;
- M is selected from the group consisting of a metal cation having a charge of $^+1$, and a metal cation group having a charge of $^+2$; and
- X is a heteroatom.

Other aspects and iterations of the invention are described more thoroughly below.

DETAILED DESCRIPTION OF THE INVENTION

The present invention provides a process for producing buprenorphine and derivatives of buprenorphine, such as a compound of Formula (II), that results in less than or equal to 0.15% of any related single individual impurity. In particular, it has been discovered that alkylating norbuprenorphine, or derivatives of norbuprenorphine, such as a compound of Formula (I), at a temperature below 60° C. in the presence of a catalytic additive results in a compound of Formula (II) that comprises less than 0.15% by weight of Impurity A. In addition, a method has been discovered for purifying the alkylating agent, a compound comprising $R^1X^1$, such that it contains less than 0.15% of an alkenyl impurity. This further inhibits Impurity A formation during the alkylation reaction. Moreover, it has been discovered that both compounds of Formula (I) and Formula (II) can be recrystallized to further reduce impurities. These improvements allow for the manufacture of a compound of Formula (II), such as buprenorphine, or derivatives thereof, to meet both USP and ICH guidelines.

Synthesis of Compounds Comprising Formula (II)

The process of the invention comprises the alkylation of an opiate compound of formula (I) to form an opiate compound of formula (II). The alkylation is performed in the presence $R^1X^1$, a carbonate source, and a catalytic additive. For purposes of illustration, Reaction Scheme 1 depicts the production of a compound comprising Formula (II) in accordance with one aspect of the invention:

(II)

wherein:
- $R^1$ is selected from the group consisting of an alkyl, a substituted alkyl, and a cycloalkyl;
- $R^2$ and $R^3$ are independently selected from the group consisting of hydrogen, hydrocarbyl and substituted hydrocarbyl;
- $R^4$ and $R^5$ are independently selected from the group consisting of hydrogen, hydrocarbyl, substituted hydrocarbyl, halogen, {—}OH, {—}NH$_2$, {—}SH, {—}SR$^{11}$, and {—}OR$^{11}$;
- $R^6$ and $R^7$ are independently selected from the group consisting of hydrogen, a protecting group, hydrocarbyl, and substituted hydrocarbyl;
- $R^8$ is selected from the group consisting of hydrogen, hydrocarbyl, and substituted hydrocarbyl;
- $R^9$, $R^{10}$, and $R^{11}$ are independently selected from the group consisting of hydrocarbyl and substituted hydrocarbyl;
- M is selected from the group consisting of a metal cation having a charge of $^+1$, and a metal cation group having a charge of $^+2$;
- X is a heteroatom; and
- $X^1$ is a halogen.

In one exemplary embodiment, $R^1X^1$ is cyclopropylmethylbromide, and the compound comprising formula (II) is buprenorphine, or a derivative of buprenorphine comprising formula (IIa):

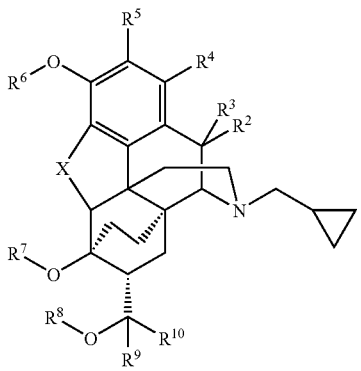

(IIa)

wherein:

$R^2$ and $R^3$ are independently selected from the group consisting of hydrogen, hydrocarbyl and substituted hydrocarbyl;

$R^4$ and $R^5$ are independently selected from the group consisting of hydrogen, hydrocarbyl, substituted hydrocarbyl, halogen, {—}OH, {—}NH$_2$, {—}SH, {—}SR$^{11}$, and {—}OR$^{11}$;

$R^6$ and $R^7$ are independently selected from the group consisting of hydrogen, a protecting group, hydrocarbyl, and substituted hydrocarbyl;

$R^8$ is selected from the group consisting of hydrogen, hydrocarbyl, and substituted hydrocarbyl;

$R^9$, $R^{10}$, and $R^{11}$ are independently selected from the group consisting of hydrocarbyl and substituted hydrocarbyl; and X is a heteroatom.

In another exemplary embodiment, a compound comprising formula (Ia), i.e. norbuprenorphine is alkylated to form an opiate compound of formula (IIb), i.e. buprenorphine. The alkylation is performed in the presence cyclopropylmethylbromide, potassium carbonate, and the catalytic additive potassium iodide. For purposes of illustration, Reaction Scheme 2 depicts the production of a compound comprising Formula (IIb) in accordance with one aspect of the invention:

Reaction Scheme 2

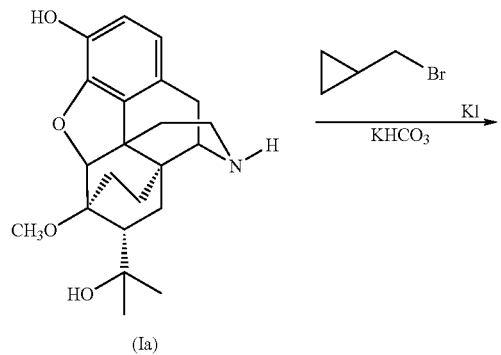

(Ia)

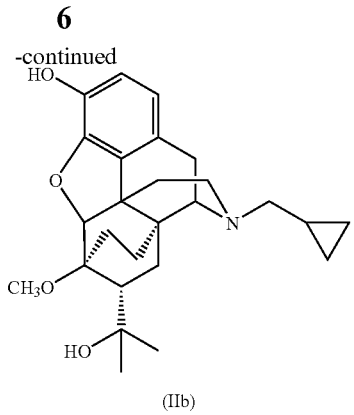

(IIb)

(a) Reaction Mixture

The process of the invention commences with formation of a reaction mixture by combining a compound comprising Formula (I), $R^1X^1$, MCO$_3$, a catalytic additive, and a solvent. A variety of compounds having Formula (I) are suitable for use in the process. In one iteration of the process, for the compound having Formula (I), X is oxygen. In another iteration, $R^7$, $R^9$, and $R^{10}$ are alkyl or substituted alkyl. In yet another iteration, $R^2$, $R^3$, $R^4$, $R^5$, $R^6$, and $R^8$ are hydrogen. In some iterations, X is oxygen; and $R^2$, $R^3$, $R^4$, $R^5$, $R^6$, and are hydrogen. In other iterations, X is oxygen; $R^7$, $R^6$, and $R^{10}$ are alkyl or substituted alkyl; and $R^2$, $R^3$, $R^4$, $R^5$, $R^6$, and $R^8$ are hydrogen. In still other iterations, X is oxygen; $R^2$, $R^3$, $R^4$, $R^5$, $R^6$, and $R^8$ are hydrogen; $R^7$ and $R^{10}$ are methyl; and $R^9$ is tertiary butyl. In an exemplary embodiment of the process, the compound having Formula (I) comprises Formula (Ia), otherwise known as norbuprenorphine.

Methods of making a compound comprising Formula (I) are known in the art. In one embodiment, a compound comprising Formula (Ia) may be synthesized by hydrolyzing 6,14-Ethenomorphinan-17-carbonitrile, 4,5-epoxy-18,19-dihydro-7-(1-hydroxy-1,2,2-trimethylpropyl)-3,6-dimethoxy-, [5α,7α(S)]-(9Cl) to norbuprenorphine. The hydrolysis reaction may comprise heating 6,14-Ethenomorphinan-17-carbonitrile, 4,5-epoxy-18,19-dihydro-7-(1-hydroxy-1,2,2-trimethylpropyl)-3,6-dimethoxy-, [5α,7α(S)]-(9Cl) in KOH and diethylene glycol to 180-200° C. The resulting norbuprenorphine may be recrystallized to reduce impurities, as described in the examples.

In addition to a compound comprising Formula (I), the reaction mixture also comprises the compound $R^1X^1$. In various iterations of the process, $X^1$ may be a halogen. For instance, in one embodiment, $X^1$ may be bromide. In another embodiment, $X^1$ may be chlorine. In other iterations of the process, $R^1$ is a cycloalkyl, such as cyclopropylmethyl. In certain embodiments, $R^1$ is a cycloalkyl and $X^1$ is selected from the group consisting of bromide and chloride. In an exemplary embodiment, $R^1$ is a cyclopropylmethyl and $X^1$ is selected from the group consisting of bromide and chloride. Typically, the molar ratio of the compound comprising Formula (I) to $R^1X^1$ is from about 1:0.5 to about 1:1.85. For instance, in some embodiments, the molar ratio is 1:0.6, 1:0.65, 1:0.7, 1:0.75, 1:0.8, 1:0.85, 1:0.9, 1:0.95, 1:1, 1:1.05, 1:1.1, 1:1.15, 1:1.2, 1:1.25, 1:1.3, 1:1.35, 1:1.4, 1:1.45, 1:1.5, 1:1.55, 1:1.6, 1:1.65, 1:1.7, 1:1.75, 1:1.8, or 1:1.85. In an exemplary embodiment, the molar ratio is from about 1:1 to about 1:1.35.

As detailed above, the $R^1X^1$ compound comprises less than 0.15% by weight of alkenyl impurity. In some embodiments, the $R^1X^1$ compound comprises less than 0.14, 0.13, 0.12, 0.11, 0.10, 0.09, 0.08, 0.07, 0.06, 0.05, 0.04, 0.03, 0.02, or 0.01% by weight alkenyl impurity. Generally speaking, the lower the alkenyl impurity, the lower the level of Impurity A in the product of the process. The alkenyl impurity may be a butenyl impurity. For instance, if $X^1$ is bromide, the alkenyl impurity may be 4-bromo-1-butene. If $X^1$ is chlorine, the alkenyl impurity may be 4-chloro-1-butene. In each of the above embodiments, X is oxygen; $R^7$, $R^9$, and $R^{10}$ are alkyl or substituted alkyl; and $R^2$, $R^3$, $R^4$, $R^5$, $R^6$, and $R^8$ are hydrogen.

If the $R^1X^1$ compound comprises greater than 0.15% percent of an alkenyl impurity, the $R^1X^1$ compound may be treated to reduce the percent of the alkenyl impurity. The method selected to reduce the impurity depends, in part, on the $R^1X^1$ compound and on the alkenyl impurity. For instance, in certain embodiments, the mixture comprising the $R^1X^1$ compound may be distilled to reduce the impurity. A method for reducing the percent of an alkenyl impurity is detailed in the examples below.

The reaction mixture further comprises a catalytic additive. Generally speaking, the catalytic additive is miscible in the reaction solvent and has a boiling point below 60° C. In one embodiment, the catalytic additive is KI (i.e. potassium iodide). In another embodiment, the catalytic additive is NaI (i.e. sodium iodide). In yet another embodiment, the catalytic additive may be CsI (i.e. cesium iodide). Typically, the molar ratio of the compound comprising Formula (I) to catalytic additive is from about 1:0.5 to about 1:2.5. For instance, in some embodiments, the molar ratio is 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4 or 1:2.5. In an exemplary embodiment, the molar ratio is from about 1:1 to about 1:1.5.

The reaction mixture may also comprise $MCO_3$. In some embodiments, M is the same metal cation used in the catalytic additive. For instance, if the catalytic additive is KI, then $MCO_3$ may be $K_2CO_3$. In contrast, if the catalytic additive is NaI, then $MCO_3$ may be NaHCO3 or $Na_2CO_3$. In other embodiments, $MCO_3$ may be $Cs_2CO_3$ or $CaCO_3$. Typically, the molar ratio of the compound comprising Formula (I) to $MCO_3$ is from about 1:0.5 to about 1:3.5. For instance, in some embodiments, the molar ratio is 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, or 1:3.5. In an exemplary embodiment, the molar ratio is from about 1:1 to about 1:2.5.

Additionally, the reaction mixture comprises a solvent. Generally speaking, the solvent should have a polarity similar to acetone, and the inorganic molecules in the reaction mixture should be soluble in the solvent. In some embodiments, the solvent may be selected from the group comprising acetone, toluene, tetrahydrofuran, acetonitrile, methyl ethyl ketone, chlorobenzene and fluorobenzene. In an exemplary embodiment, the solvent is acetone. In another exemplary embodiment, $R^1X^1$ is cyclopropylmethylbromide, $MCO_3$ is potassium bicarbonate, the catalytic additive is potassium iodide, the solvent is acetone, and the alkene impurity comprises 4-bromo-1-butene.

After the reaction mixture is formed, the mixture is typically heated, as described in the examples. Generally speaking, the mixture is heated to a temperature less than about 60° C. but greater than about 50° C. For instance, the mixture may be heated to a temperature of less than 59° C., 58° C., 57° C., 56° C., 55° C., 54° C., 53° C., 52° C., or 51° C. Keeping the temperature below about 60° C. reduces the formation of Impurity A. The mixture may be heated for between about for about 4 to about 15 hours. In some embodiments, the mixture may be heated for about 4, 5, 6, 7, 8, 9, 10, 11, 12, 13, 14, or 15 hours. In other embodiments, the mixture may be heated for between about 5 and about 10 hours.

After heating, the product may be precipitated by adding water. The precipitate may be filtered and washed. In some instances, the precipate may be washed with acetonitrile. In certain embodiments, the product may be recrystallized as described in more detail in section (b) and in the examples below. In some embodiments, the precipitate need not be washed prior to recrystallization.

Generally speaking, the yield of a compound comprising Formula (II) from the process of the invention is between about 65% and about 100%. In certain embodiments, the yield is between about 84% to about 95%. In some embodiments, the yield is at least 84%, 85%, 86%, 87%, 88%, 89%, 90%, 91%, 92%, 93%, 94%, 95%, 96%, 97%, 98%, or 99%.

In each of the above embodiments, the product formed in a process of the invention comprises less than 0.15% by weight of a related individual impurity. Non-limiting examples of possible impurities may include Impurity A, Impurity D, or Impurity E. In one embodiment, the product comprises less than 0.15% by weight of Impurity A. Impurity A, otherwise known as (2S)-2-[17-(but-3-enyl)-4,5α-epoxy-3-hydroxy-6-methoxy-6α,14-ethano-14α-morphinan-7α-yl]-3,3-dimethylbutan-2-ol, has the following structure:

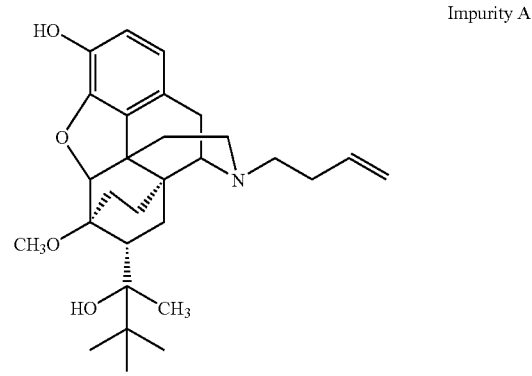

Impurity A

In some embodiments, the product comprises less than 0.14, 0.13, 0.12, 0.11, 0.10, 0.09, 0.08, 0.07, 0.06, 0.05, 0.04, 0.03, 0.02, or 0.01% by weight of Impurity A.

In another embodiment, the product comprises less than 0.15% by weight of Impurity D. Impurity D, otherwise known as 6,14-Ethenomorphinan-7-methanol, 17-(cyclopropylmethyl)-α-(1,1-dimethylethyl)-4,5-epoxy-3-hydroxy-6-methoxy-α-methyl-, (αS,5α,7α), has the following structure:

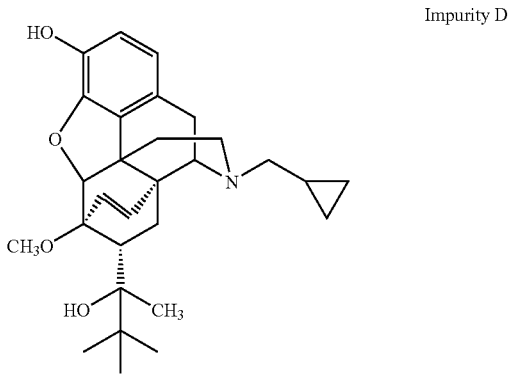

Impurity D

The bridge containing the double bond has cis chemistry. In some embodiments, the product comprises less than 0.14, 0.13, 0.12, 0.11, 0.10, 0.09, 0.08, 0.07, 0.06, 0.05, 0.04, 0.03, 0.02, or 0.01% by weight of Impurity D.

In yet another embodiment, the product comprises less than 0.15% by weight of impurity E. Impurity E, otherwise known as (2S)-2-[17-(cyclopropylmethyl)-4,5α-epoxy-3,6-dihydroxy-6α,14-ethano-14α-morphinan-7α-yl]-3,3-dimethylbutan-2-ol (6-O-desmethylbuprenorphine), has the following structure:

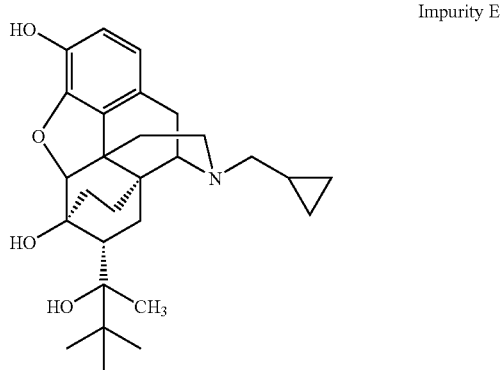

Impurity E

In some embodiments, the product comprises less than 0.14, 0.13, 0.12, 0.11, 0.10, 0.09, 0.08, 0.07, 0.06, 0.05, 0.04, 0.03, 0.02, or 0.01% by weight of Impurity E. In certain embodiments, the product comprises less than 0.15, 0.14, 0.13, 0.12, 0.11, 0.10, 0.09, 0.08, 0.07, 0.06, 0.05, 0.04, 0.03, 0.02, or 0.01% by weight of any combination of Impurity A, D or E.

(b) Recrystallization Process to Reduce Impurities

To further reduce impurities, the product of the process described above may be recrystallized. Recrystallization, as opposed to chromatographic separation, may be used to further reduce impurities because the process of the invention, as described above, results in a product with low impurity levels. Avoiding chromatographic separations decreases the time and money involved in producing buprenorphine.

The compound comprising Formula (II) or (IIa) may be precipitated from the reaction mixture with water, as described in the examples. Briefly, water is added to the cooled reaction mixture. The resulting mixture is heated to help dissolve any water soluble impurities. In some embodiments, the mixture is heated to less than 60° C. but greater than 50° C. The mixture may then be cooled to precipitate the product. In certain embodiments, the mixture may be cooled to about 20° C. to about 30° C., and then filtered. The reactor and the solid may then be washed, for instance, with water or acetonitrile. This filtered product may then be recrystallized to reduce impurities.

The recrystallization process generally comprises dissolving the filtered product in a recrystallization solvent. Suitable recrystallization solvents may include acetonitrile alone or in combination with an alcohol, such as methanol or ethanol. In an exemplary embodiment, the recrystallization solvent is acetonitrile. The solution may be heated to aid in the dissolution of the filtered product. Generally speaking, the solution may be heated up to the boiling point of the solvent. For instance, in some embodiments, the solution may be heated to a temperature between about 65° C. to about 85° C. In other embodiments, the solution may be heated to about 65, 66, 67, 68, 69, 70, 71, 72, 73, 74, 75, 76, 77, 78, 79, 80, 81, 82, 83, 84, or 85° C. In still other embodiments, the solution may be heated to about 75° C. to about 80° C. In certain embodiments, the solution may be clarified. Generally speaking, if the solution is clarified, the filtration set up should be rinsed with warm solvent to recover any remaining product.

After the product is dissolved in the recrystallization solvent, the solution is distilled to remove an amount of the solvent. For instance, in some embodiments, the solution is distilled to remove about 50, 55, 60, 65, 70, or 75% of the solvent. In other embodiments, the solution is distilled to remove about 60% to about 70% of the solvent. In an exemplary embodiment, about 68% of the solvent is removed. After distillation, the solution is cooled to less than about 15, 14, 13, 12, 10, 9, 8, 7, 6, 5, or 4° C. and stirred for about 10, 15, 20, 25, 30, 35, 40, or 45 minutes. The solution is then filtered and washed with cold solvent.

Typically, the recrystallization yield is greater than 50%. In some embodiments, the yield is at least 50%, 55%, 60%, 65%, 70%, 75%, 80%, 85%, 90%, 95%, or greater than 95%. In other embodiments, the yield is about 90% to about 94%. The recrystallized product is generally at least about 95%, 96%, 97%, 98%, 99%, or greater than 99% pure. After the recrystallization, the percent of Impurity A is generally less than 0.15%. In some embodiments, the percent of Impurity A is less than 0.14, 0.13, 0.12, 0.11, 0.10, 0.09, 0.08, 0.07, 0.06, 0.05, 0.04, 0.03, 0.02, or 0.01% by weight. Similarly, after recrystallization, the percent of Impurity E is usually less than 0.15%. In certain embodiments, the percent of Impurity E is less than 0.14, 0.13, 0.12, 0.11, 0.10, 0.09, 0.08, 0.07, 0.06, 0.05, 0.04, 0.03, 0.02, or 0.01% by weight. In addition, the percent of Impurity D may be less than 0.15%.

The compounds described herein (e.g., comprising any of Formulas (I), (II), or (IIa)) or any of the intermediates detailed herein may have a (−) or (+) stereochemistry configuration with respect to the rotation of polarized light. More specifically, C-5 and C-6 typically has an R configuration, while C-7, C-9, C-13, and C-14 may have an R or an S configuration. The compounds formed by the processes of the invention comprise morphinans. For purposes of illustration, the ring atoms of a morphinan compound are numbered as diagrammed below.

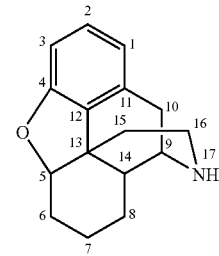

In particular, the compounds described herein may comprise chiral centers at positions C-7, C-9, C-13, and C-14. For these compounds, the stereochemistry for C-7, C-9, C-13, and C-14 may be selected from the group consisting of RRSS, SSRR, SRSS, and RSRR. In this iteration, C15 and C16 carbons are both either on the alpha face of the molecule or the beta face of the molecule. In an exemplary embodiment, a compound of Formula (II) is (−) buprenorphine.

The invention also encompasses use of pharmaceutically acceptable salts of any of the compounds described herein. Pharmaceutically acceptable cations include metallic ions and organic ions. More preferred metallic ions include, but are not limited to appropriate alkali metal salts, alkaline earth metal salts and other physiologically acceptable metal ions.

Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

DEFINITIONS

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen which, subsequent to the reaction for which protection is employed, may be removed without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various iterations of the invention.

Example 1

Alkylation of Buprenorphine in Acetone

Table 1A below lists the reactants for the alkylation reaction.

TABLE 1A

| Reagent | MW | g | volume | moles | equivalents |
|---|---|---|---|---|---|
| Norbuprenorphine | 413.6 | 8.00 | | 0.0193 | 1.0 |
| $KHCO_3$ | 100.12 | 4.25 | | 0.0425 | 2.2 |
| (Bromomethyl)cyclopropane | 135.0 | 3.39 | | 0.0251 | 1.30 |
| Acetone | | | 100 mL | | |
| KI | 166.01 | 4.58 | | 0.0276 | 1.1, to CPM-Br |
| d.i. water | | 0.8 | 0.8 mL | | |
| Work-up water | | | 160 mL | | |

A mixture of 8.0 g of norbuprenorphine, 4.25 g of $KHCO_3$, 4.58 g (1.1 eq to bromide) of KI and 95 mL of acetone plus 0.8 mL water is charged to a 500 mL flask with a mechanical stirrer and a condenser. Then 3.39 g of bromomethylcyclopropane (d 1.392) is measured out into a stoppered container and washed into the reaction flask with the remaining 5 mL of acetone. The mixture is refluxed under nitrogen for 6-8 hours. If TLC indicates incomplete reaction, it is refluxed 2 hours further, then cooled to room temperature.

To the stirred reaction mixture 160 mL of water is added dropwise during 15-40 minutes. The mixture is heated to 55-58° C. It is stirred at that temperature for 20 minutes and then allowed to cool to 20-30° C. The mixture is filtered. The reactor and solid is washed with water (2×30 ml, about 4 ml per g of starting norbuprenorphine in each wash). The vacuum is turned off and 30 mL of acetonitrile is poured onto the solid and allowed to stand there for a minute. Vacuum is applied to the funnel again and air is allowed to draw through for five minutes. The sample is dried to a constant weight. The yield is 90%, with a range of 89-91% in lab examples. With this method of isolation, the crude product has been over 93% w/w purity. It is then recrystallized to remove any remaining impurities. The crude product, air dried, may be carried on to the Example 4 step without drying, as long as the loss on drying is calculated and is used for the Example 4 procedure. Crude products had these purities when cyclopropylmethyl bromide (CPM-Br) with sufficient purity (three purities shown) was used:

TABLE 1B

| | Alkylation Results in Acetone | | | |
|---|---|---|---|---|
| Sample # | Buprenorphine w/w % | Norbuprenorphine w/w % | Level of 4-bromo-1-butene | Impurity A w/w % |
| 2 | 74.15 | 0.70 | 0.33% | 0.17 |
| 3 | 81.53 | 0.08 | 0.14% | 0.03 |
| 4 | 96.00 | 0..42 | 0.07% | 0.017 |

Further examples were run with the lot of cyclopropylmethylbromide containing 0.07% 4-bromo-1-butene:

TABLE 1C

| | Further Alkylation Examples in Acetone | | |
|---|---|---|---|
| Sample # | Buprenorphine Assay | Impurity A | Crude yield |
| 5 | 99.46% | 0.04% | 90.5% |
| 6 | 99.65% | 0.05% | 89.0% |
| 7 | 96.82% | 0.03% | 89.5% |
| 8 | 93.51% | 0.014% | 89.8% |
| 9 | 97.08% | 0.010% | 89.7% |
| 10 | 101.13% | 0.009% | 88.5% |
| 11 | 96.09% | 0.02% | 91.0% |

In another example, using extraction, is as follows: a mixture of 4.04 g of norbuprenorphine, 2.14 g of $KHCO_3$, 2.24 g of KI, 1.2 mL of bromomethylcyclopropane and 60 mL of acetone was refluxed for 6.5 h and then stirred overnight. To the mixture was added 80 mL of water to give a precipitate. Acetone was distilled out to a head temperature of 70° C. The pot was cooled to room temperature and 80 mL dichloromethane was added with stirring. Layers were separated. The water was extracted with 10 mL dichloromethane. To the combined dichloromethane extracts in a clean flask was added 55 mL of acetonitrile. The mixture was distilled to a head temperature of 74° C., collecting 80 mL. At this point some solid was seen. The mixture was allowed to cool to room temperature and filtered. The flask and solid were washed with 5 mL acetonitrile. The solid was dried in vacuo to 3.19 g (70-71%). HPLC analysis indicated 99.2% buprenorphine, 0.05% Impurity A and 0.39% norbuprenorphine. The mother liquor in acetonitrile had 4% norbuprenorphine and 60% buprenorphine. This material would need to be recrystallized once more by the Example 4 method to give passing material with all impurities under 0.15%.

Example 2

Alkylation of Buprenorphine in DMF

This example shows the best product obtained from a reaction in DMF, which was of similar purity to Example 1 above. The cyclopropylmethyl bromide was the same in both Example 1 and this example (0.07% impurity). Complete reaction was only obtained at 85° C. Reagents are shown in Table 2A below.

TABLE 2A

| Reagent | MW | g | volume | moles | equivalents |
|---|---|---|---|---|---|
| Norbuprenorphine | 413.5 | 5.05 | | 0.0122 | |
| $NaHCO_3$ | 84.0 | | | | |
| (Bromomethyl)cyclopropane | 135.0 | 2.23 | 1.6 mL | 0.0165 | 1.35 |
| DMF | | | 20 mL | | |
| Water | | | 200 mL | | |

A mixture of the 5.05 g of norbuprenorphine, 20 mL of DMF and 2.00 g $NaHCO_3$ was stirred and heated to 62° C. At this point the solids were mixed and partially dissolved. The cyclopropylmethyl bromide, 1.6 mL, was added (d 1.392). The mixture was taken to 85° C. and kept there for 5.5 hours. It was allowed to cool and poured slowly into a separate flask, mechanically stirred, with 75 mL water. Some of the product may be slightly gummy solid, especially on the stirrer blade. The reaction flask was rinsed with 1 mL DMF twice into the same. The solid obtained was filtered and washed with 50 mL water. [In some other trials, dried material after this wash can be taken directly to the hydrochloride, if it appears to be a good solid]. This batch was scooped back to the same flask and boiled with 75 mL of water briefly, then allowed to stir and cool, to remove some residual DMF. Filtration gave a brown solid, 5.42 g (94% yield) after drying in vacuo. Area % purity was 89.5%, Impurity A was 0.16% and norbuprenorphine 0.48%. The material was not recrystallized.

There are further examples of the reaction in DMF with varying levels of the butenyl impurity resulting in a variable amount of Impurity A. These are shown in the table below.

TABLE 2B

Alkylation Results in Dimethylformamide

| Sample # | Buprenorphine Area % | Norbuprenorphine Area % | Level of 4-bromo-1-butene | Impurity A Area % |
|---|---|---|---|---|
| 12 | 89.08% | 2.22 | 0.33% | 0.19% |
| 13 | 82.34% | 2.05% | 0.33% | 0.59% |
| 14 | 90.40% | 0.16% | 0.33% | 0.34% |
| 15 | 99.9% | none | 0.14% | 0.12% |
| 16 | 98.13% | 0.36% | 0.14% | 0.12% |

Example 3

Comparison of Levels of Impurity A

Alkylations of buprenorphine were conducted with various lots of bromomethylcyclopropane (CPMB). The different lots had varying levels of the alkenyl impurity 4-bromo-1-butene. The impurity in the CPMB alkylates in a side reaction and results in varying levels of Impurity A in the buprenorphine, as shown in the reaction scheme below:

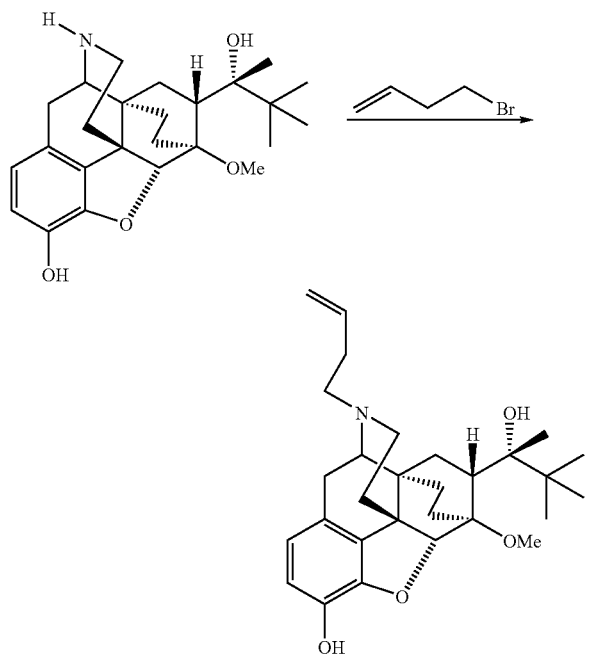

Experimental data showed that the amount of Impurity A produced is statistically related to the level of the butenyl impurity in the alkylating agent (e.g. CPMB). Lower levels of the butenyl impurity result in lower Impurity A levels, as the data in Table 3 shows. In particular, when Lot 26 was used, and comprised a butenyl impurity level of 0.14%, the acetone alkylations yielded Impurity A levels of between 0.05 and 0.06%. In contrast, using the same lot, but running the alkylation in DMF, yielded the higher Impurity A level of 0.12%.

TABLE 3

| Bromide | Level of 4-bromo-1-butene | Level of Impurity A |
|---|---|---|
| Alkylations in Acetone | | |
| Lot 2003 | 0.32% | 0.19 |
| | | 0.12 |
| | | 0.05 |
| | | 0.2 |
| | | 0.10 |
| Lot 26 | 0.14% | ND |
| | | 0.05 |
| | | 0.05 |
| | | 0.06 |
| Lot 117 | 0.33% | 0.16 |
| | | 0.11 |
| | | 0.10 |
| | | 0.13 |
| | | 0.15 |
| Lot 9520 | 0.69% | 0.26 |
| | | 0.21 |
| Alkylations in DMF | | |
| Lot 117 | 0.33% | 0.19 |
| | | 0.59 |
| | | 0.34 |
| Lot 26 | 0.14% | 0.12 |
| | | 0.12 |

Example 4

Recrystallization of Buprenorphine

The alkylation process yields a crude product of 97-99% purity containing 0.1% or less of Impurity A with an acceptable alkylating agent. This relatively clean crude product allows for recrystallization of the crude solid and therefore avoids the need for chromatographic separations. Avoiding a chromatographic separation reduces both manufacturing costs and time. Recrystallization involves the dissolution of buprenorphine in acetonitrile followed by distillation to optimize the recovery. The recovery after recrystallization is typically 90-92%. The recrystallization of the crude buprenorphine can remove 17-20% of Impurity A. If a second recrystallization is performed, the level of Impurity A can be reduced by another 6%. In addition, Impurity E may be removed by recrystallization.

One example of a recrystallization of a crude buprenorphine base that had a Impurity A level of 0.02% is as follows. The base (45.05 g) is added to 1295 ml of Acetonitrile charged to a 2-L jacketed reactor with a mechanical stirrer and a condenser. The mixture is heated to 75-80° C. to dissolve the solids. Clarification may be required. If so, a rinse of warm acetonitrile is also required to recover the buprenorphine in the filtration set up. The solution is then set up for distillation to remove 60-70% of the solvent used with a target of 68% desired for optimal recovery. For this example 890 mL was distilled from the batch. The batch is then cooled to <10° C. and stirred for 30 minutes. The batch is filtered and washed with 75 mL Acetonitrile (cold). The sample is dried to a constant weight. The yield is 94%, with a range of 90-94% in lab examples. The weight assay of Buprenorphine is 99.77% with Impurity A at 0.014%. The sum of all other impurities is 0.37 by area percent. The results are in Table 4A below.

TABLE 4A

Recrystallization Results of Buprenorphine

| Sample | Starting Level of Impurity A | Impurity A after 1st Recrystallization | Impurity A after 2nd Recrystallization |
|---|---|---|---|
| 18 | 0.19% | 0.16% | 0.15% |
| 19 | 0.04% | 0.03% | 0.03% |
| 20 | 0.18% | 0.10% | 0.10% |

Results of additional recrystallizations are shown below in Tables 4B and 4C.

TABLE 4B

| Starting Grams (as is) | Assay (w/w %) | Grams at 100% | Grams Recovered | Assay (w/w %) | Grams at 100% | Percent Recovery |
|---|---|---|---|---|---|---|
| 53.92 | 98.67 | 53.20 | 46.40 | 99.28 | 46.06 | 86.58 |
| 52.52 | 98.11 | 51.53 | 44.92 | 98.39 | 44.19 | 85.77 |
| 50.96 | 96.82 | 49.34 | 43.90 | 99.11 | 43.51 | 88.19 |
| 51.03 | 93.51 | 47.72 | 44.76 | 99.36 | 44.47 | 93.20 |
| 50.98 | 95.52 | 48.70 | 44.45 | 98.26 | 43.67 | 89.69 |
|  | 97.29 (avg) |  |  | 98.89 (avg) |  | 88.68 (avg) |

TABLE 4C

| Norbuprenorphine (Wt. %) | Buprenorphine (Wt. %) | Impurity A (Wt. %) | Compound E (Area %) |
|---|---|---|---|
| 0.050 | 99.28 | 0.013 | 0.02 |
| 0.044 | 98.39 | 0.015 | 0.02 |
| 0.001 | 99.15 | 0.015 | 0.02 |
| 0.001 | 99.36 | 0.015 | 0.02 |
| 0.001 | 98.26 | 0.015 | 0.02 |
| 0.019 (AVG) | 98.89 (AVG) | 0.015 (AVG) | 0.02 (AVG) |

Example 5

Distillation of CPMB

The synthesis of CPMB is typically performed at reduced temperatures to obtain selectivity to the desired product. The synthesis results in the formation of 2 side products, shown in the reaction scheme below:

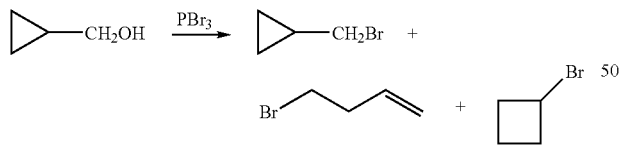

The bromocyclobutane side product is unreactive, while the 4-bromo-1-butene side product should be below 0.5% for use in the alkylations described above. If the CPMB is not pure enough (generally less than 0.5% of the butenyl impurity) the CPMB can be purified. CPMB and the butenyl impurity have a narrow boiling point range, hence fractional distillation was used to separate the two. The distillation system utilized a >5 plate Oldershaw distillation column with a controlled splitter apparatus. The distillation is performed under reduced pressure and low temperature in a batch process. The recovery is typically 45-64%, operated at 39-40° C. and 47-52 millibar. The butenyl bromide is distilled forward and the CPMB with increased purity remains in the distillation vessel. Split ratios of 1.5:1 to 4:1 may be used. Results of the distillation process are shown in Table 5 below.

TABLE 5

| Initial Charge (g) | Purified (g) | Initial Impurity (%) | Final Impurity (%) | Purity (%) | Recovery (%) |
|---|---|---|---|---|---|
| 306.24 | 130.89 | 2.29 | 0.25 | 98.67 | 42.74 |
| 451.71 | 202.24 | 0.55 | 0.13 | 99.49 | 44.77 |
| 208.80 | 102.17 | 1.18 | 0.70 | 97.91 | 48.93 |
| 584.33 | 374.09 | 0.69 | 0.16 | 99.33 | 64.02 |
| 4176 | 1785 | 0.84 | 0.15 | 99.2 | 42.74 |
| 5568 | 2728 | 0.89 | 0.14 | 99.2 | 48.99 |
| 6264 | 3065 | 0.92 | 0.15 | 98.9 | 48.93 |

Example 6

Recrystallization of Norbuprenorphine

Due to the harsh conditions (high temperature and caustic environment) of the hydrolysis reaction that produces norbuprenorphine, the norbuprenorphine may be recrystallized. The process involves dissolution of crude product in a two component system (methanol and acetonitrile) followed by distillation to optimize recovery. The typical recovery is between 89-92%. The alkene that ultimately forms impurity D is partially removed from the mother liquor during this recrystallization. The recrystallization increases the purity of norbuprenorphine is increased to >96%. The recrystallization can also remove a high amount of 3-O-methylnorbuprenorphine to less than <1% (initially 13% by area percent). The results are shown in Table 6 below.

TABLE 6

| Hydrolysis reaction (g)@100% | Isolated (g) | Wt % | Recovery (%) | Comments |
|---|---|---|---|---|
| 27.76 | 26.10 | 95.04 | 89.36 | Starting purity = 85.14% |
| 36.34 | 35.82 | 94.09 | 92.74 | Starting purity = 88.23% |
| 43.98 | 40.74 | 93.80 | 86.89 | Starting purity = 71.01% |
| 54.03 | 53.32 | 97.04 | 95.73 | Starting purity = 92.47% |
| 19.06 | 19.49 | 96.08 | 97.19 | Starting purity = 89.49% |
| 19.42 | 19.38 | 96.87 | 93.21 | Starting purity = 90.60% |

What is claimed is:

1. A process for the preparation of a compound of Formula (II), the process comprising:
    (a) forming a reaction mixture by combining a compound of Formula (I) with $MCO_3$, a catalytic additive, and $R^1X^1$, the amount of alkenyl impurity comprising $R^1X^1$ being less than 0.15% by weight; and
    (b) heating the reaction mixture to a temperature of less than 60° C. to form the compound of Formula (II) according to the following reaction scheme:

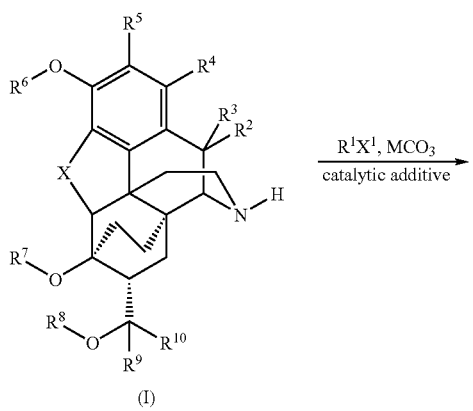

(I)

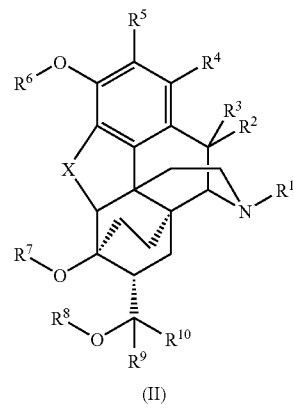

(II)

wherein;
- $R^1$ is selected from the group consisting of an alkyl, a substituted alkyl, and a cycloalkyl;
- $R^2$ and $R^3$ are independently selected from the group consisting of hydrogen, hydrocarbyl and substituted hydrocarbyl;
- $R^4$ and $R^5$ are independently selected from the group consisting of hydrogen, hydrocarbyl, substituted hydrocarbyl, halogen, {—}OH, {—}NH$_2$, {—}SH, {—}SR$^{11}$, and {—}OR$^{11}$;
- $R^6$ and $R^7$ are independently selected from the group consisting of hydrogen, a protecting group, hydrocarbyl, and substituted hydrocarbyl;
- $R^8$ is selected from the group consisting of hydrogen, hydrocarbyl, and substituted hydrocarbyl;
- $R^9$, $R^{10}$, and $R^{11}$ are independently selected from the group consisting of hydrocarbyl and substituted hydrocarbyl;
- M is selected from the group consisting of a metal cation having a charge of $^+1$, and a metal cation group having a charge of $^+2$;
- X is oxygen; and
- $X^1$ is a halogen.

2. The process of claim 1, wherein $R^1$ is cyclopropylmethyl, $X^1$ is a halogen selected from the group consisting of bromide and chloride; $R^7$, $R^9$, and $R^{10}$ are alkyl or substituted alkyl; and $R^2$, $R^3$, $R^4$, $R^5$, $R^6$, and $R^8$ are hydrogen; the catalytic additive is selected from the group consisting of potassium iodide and sodium iodide; and MCO$_3$ is potassium bicarbonate.

3. The process of claim 1, wherein the molar ratio of the compound of Formula (I) to catalytic additive is from about 1:1 to about 1:1.5; the molar ratio of the compound of Formula (I) to $R^1X^1$ is from about 1:1 to about 1:1.35; and the molar ratio of the compound of Formula (I) to MCO$_3$ is from about 1:1 to about 1:2.5.

4. The process of claim 1, further comprising conducting the reaction in the presence of the solvent acetone.

5. The process of claim 1, wherein $R^1X^1$ is cyclopropylmethylbromide, MCO$_3$ is potassium bicarbonate, the catalytic additive is potassium iodide, the reaction is conducted in the presence of acetone, and the alkene impurity comprises 4-bromo-1-butene.

6. The process of claim 1, further comprising precipitating the compound of Formula (II) from the reaction mixture in step (b) and then recrystallizing the precipitate to yield the compound of Formula (II).

7. The process of claim 6, wherein the precipitate of Formula (II) is dissolved in the solvent acetonitrile.

8. The process of claim 7, wherein at least 60% by weight of the acetonitrile is removed by distillation prior to the recrystallization of the compound of Formula (II).

9. A process for the preparation of a compound of Formula (IIa), the process comprising:
(a) forming a reaction mixture by combining a compound of Formula (I) with MCO$_3$, a catalytic additive, and cyclopropylmethylbromide, the cyclopropylmethylbromide comprising less than 0.15% by weight of 4-bromo-1-butene; and
(b) heating the reaction mixture to a temperature of less than 60° C. to form the compound of Formula (IIa) according to the following reaction scheme:

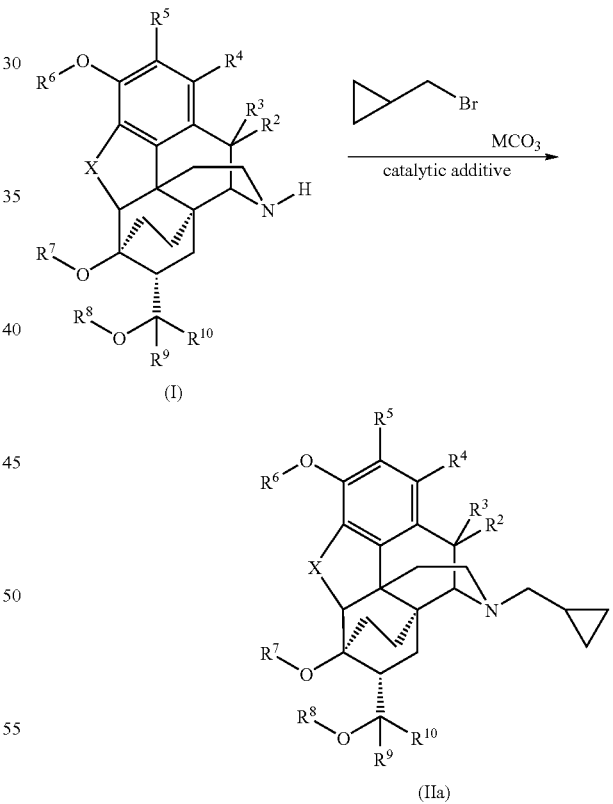

wherein:
- $R^2$ and $R^3$ are independently selected from the group consisting of hydrogen, hydrocarbyl and substituted hydrocarbyl;
- $R^4$ and $R^5$ are independently selected from the group consisting of hydrogen, hydrocarbyl, substituted hydrocarbyl, halogen, {—}OH, {—}NH$_2$, {—}SH, {—}SR$^{11}$, and {—}OR$^{11}$;

R⁶ and R⁷ are independently selected from the group consisting of hydrogen, a protecting group, hydrocarbyl, and substituted hydrocarbyl;

R⁸ is selected from the group consisting of hydrogen, hydrocarbyl, and substituted hydrocarbyl;

R⁹, R¹⁰, and R¹¹ are independently selected from the group consisting of hydrocarbyl and substituted hydrocarbyl;

M is selected from the group consisting of a metal cation having a charge of ⁺1, and a metal cation group having a charge of ⁺2; and X is oxygen.

10. The process of claim 9, wherein R⁷, R⁹, and R¹⁰ are alkyl or substituted alkyl; and R², R³, R⁴, R⁵, R⁶, and R⁸ are hydrogen.

11. The process of claim 9, wherein:
R², R³, R⁴, R⁵, R⁶, and R⁸ are hydrogen;
R⁷ and R¹⁰ are methyl; and,
R⁹ is tertiary butyl.

12. The process of claim 9, further comprising conducting the reaction in the presence of the solvent acetone.

13. The process of claim 12, wherein the molar ratio of the compound of Formula (I) to catalytic additive is from about 1:1 to about 1:1.5; the molar ratio of the compound of Formula (I) to cyclopropylmethylbromide is from about 1:1 to about 1:1.35; and the molar ratio of the compound of Formula (I) to MCO₃ is from about 1:1 to about 1:2.5.

14. The process of claim 13, wherein MCO₃ is potassium bicarbonate, the catalytic additive is potassium iodide, and the reaction is conducted in the presence of acetone.

15. The process of claim 9, wherein the cyclopropylmethylbromide comprises less than 0.05% by weight of 4-bromo-1-butene.

16. The process of claim 9, wherein the product formed comprises less than 0.15% by weight of an impurity selected from the group consisting of (2S)-2-[17-(but-3-enyl)-4,5α-epoxy-3-hydroxy-6-methoxy-6α,14-ethano-14α-morphinan-7α-yl]-3,3-dimethylbutan-2-ol, 6,14-Ethenomorphinan-7-methanol, 17-(cyclopropylmethyl)-α-(1,1-dimethylethyl)-4,5-epoxy-3-hydroxy-6-methoxy-α-methyl-, (αS,5α,7α), (2S)-2-[17-(cyclopropylmethyl)-4,5α-epoxy-3,6-dihydroxy-6α,14-ethano-14α-morphinan-7α-yl]-3,3-dimethylbutan-2-ol (6-O-desmethylbuprenorphine), and combinations thereof.

17. The process of claim 16, wherein the product formed comprises less than 0.15% by weight of (2S)-2-[17-(but-3-enyl)-4,5α-epoxy-3-hydroxy-6-methoxy-6α,14-ethano-14α-morphinan-7α-yl]-3,3-dimethylbutan-2-ol.

18. The process of claim 9, further comprising precipitating the compound of Formula (IIa) from the reaction mixture in step (b) and then recrystallizing the precipitate to yield the compound of Formula (IIa).

19. The process of claim 18, wherein the precipitate of Formula (II) is dissolved in the solvent acetonitrile.

20. The process of claim 19, wherein at least 60% by weight of the acetonitrile is removed by distillation prior to the recrystallization of the compound of Formula (II).

\* \* \* \* \*